United States Patent
Katsushima et al.

[11] 3,944,587
[45] Mar. 16, 1976

[54] HYDROXYPOLYFLUOROALKYL-CONTAINING SILANE DERIVATIVES AND MANUFACTURING THE SAME

[75] Inventors: Atsuo Katsushima, Takarazuka; Shinichi Imazu; Shoshin Fukui, both of Toyonaka; Akitoshi Iwatani, Suita; Tadashi Akazawa, Ibaragi, all of Japan

[73] Assignee: Daikin Kogyo Kabushiki Kaisha, Osaka, Japan

[22] Filed: Apr. 10, 1974

[21] Appl. No.: 459,726

[30] Foreign Application Priority Data
Apr. 14, 1973  Japan................. 48-42402

[52] U.S. Cl..... 260/448.8 R; 260/448.2 N; 252/8.6; 106/13
[51] Int. Cl.²..... C07F 7/04; C07F 7/10; C07F 7/18
[58] Field of Search............... 260/448.8 R, 448.2 N

[56] References Cited
UNITED STATES PATENTS
3,317,577  5/1967  Ryan............................ 260/448.2 N
3,560,543  2/1971  Rueddemann............... 260/448.2 N

*Primary Examiner*—Paul F. Shaver
*Attorney, Agent, or Firm*—Armstrong, Nikaido & Wegner

[57] ABSTRACT

A hydroxypolyfluoroalkyl-containing silane derivative having the formula

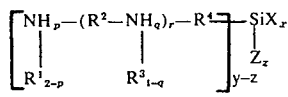

wherein each of $R^1$ and $R^3$ is alkyl; each of $R^2$ and $R^4$ is alkylene; X is alkoxyl, alkyl, hydroxy, chlorine or hydrogen and at least one of the groups represented by X is alkoxyl, hydroxy, chlorine or hydrogen; $p$ is 0 to 2, $q$ is 0 or 1, $r$ is 0 to 5, $y$ is 1 or 2 and $x$ is 2 or 3, provided that the sum of $p$ and $qr$ is at least 1 and the sum of $x$ and $y$ is 4; $z$ is 1 or 2 and is equal to or less than $y$; and Z is a group represented by

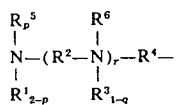

wherein $R^1$, $R^2$, $R^3$, $R^4$, $p$, $q$ and $r$ are the same as above and each of $R^5$ and $R^6$ is a hydrogen or

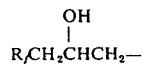

and at least one of the groups represented by $R^5$ and $R^6$ is

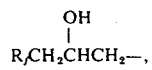

$R_f$ being a perfluoroalkyl group: the above compound being useful as water- and oil-repellent agent.

13 Claims, No Drawings

HYDROXYPOLYFLUOROALKYL-CONTAINING SILANE DERIVATIVES AND MANUFACTURING THE SAME

This invention relates to novel hydroxypolyfluoroalkyl-containing silane derivatives and the manufacture thereof.

An object of this ivention is to providee novel hydroxypolyfluoroalkyl-containing silane derivatives especially useful as water- and oil-repellent agents and a process for producing the above derivatives.

Another object of the invention is to provide water- and oil-repellent compositions containing the above derivatives as an effective ingredient.

These and other objects and advantages of the present invention will be apparent from the following description.

The hydroxypolyfluoroalkyl-containing silane derivatives of the present invention are those represented by the following formula:

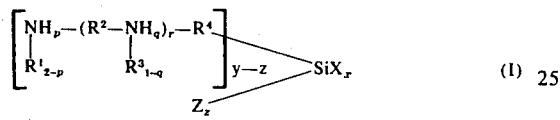
(I)

wherein each of $R^1$ and $R^3$ is an alkyl group having 1 to 5 carbon atoms; each of $R^2$ and $R^4$ is an alkylene group having 1 to 5 carbon atoms; X is an alkoxyl group having 1 to 5 carbon atoms, alkyl group having 1 to 5 carbon atoms, hydroxyl group, chlorine atom or hydrogen atom and at least one of the groups represented by X is an alkoxyl group having 1 to 5 carbon atoms, hydroxyl group, chlorine atom or hydrogen atom; $p$ is zero or an integer of 1 or 2, $q$ is zero or one, $r$ is zero or an integer of 1 to 5, $y$ is an integer of 1 or 2 and $x$ is an integer of 2 or 3, provided that the sum of $p$ and $q.r$ is at least 1 and the sum of $x$ and $y$ is 4; $z$ is an integer of 1 or 2 equal to or less than that represented by $y$; and Z is a group represented by

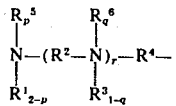

wherein $R^1$, $R^2$, $R^3$, $R^4$, $p$, $q$ and $r$ are the same as defined above and each of $R^5$ and $R^6$ is a hydrogen atom or

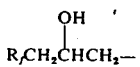

and at least one of the groups represented by $R^5$ and $R^6$ is

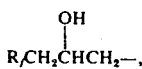

$R_f$ being a straight-chain or branched-chain perfluoroalkyl group having 3 to 21 carbon atoms; each of said $R^2$, $R^4$, $R^5$, $R^6$ and X being different or same when plural in number.

The silane derivatives of the present invention are soluble in various organic solvents and can impart excellent water- and oil-repellency to versatile porous and non-porous materials such as cloth, paper, leather, metal, glass, plastics, etc. Especially, the articles treated with the present compounds display durable water- and oil-repellency with a high order of antifriction property. This durability is ensured even if the article to be treated is made of non-porous inorgnic materials. The reason why the coatings formed on the articles treated with the present compounds have excellent durability and antifriction property has not been made clear yet, but it is supposedly attributable to the fact that the present compounds have in the molecule functional groups represented by X and functional alcoholic hydroxyl groups.

Preferable silane derivatives of the inventon are those having the formula

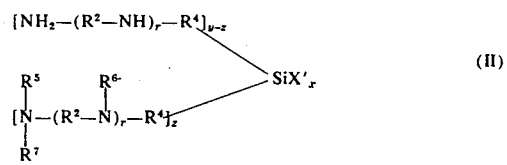
(II)

wherein $R^2$, $R^4$, $R^5$, $R^6$, $r$, $x$, $y$ and $z$ are the same as defined above, $R^7$ is a hydrogen atom or

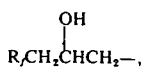

$R_f$ being the same as defined above and X′ is an alkoxyl group having 1 to 5 carbon atoms or an alkyl group having 1 to 5 carbon atoms and at least one of the groups represented by X′ is an alkoxyl group having 1 to 5 carbon atoms.

Among these particularly preferable are (1) those having the formula (II) above in which at least one of groups represented by $R^5$ and $R^7$ is

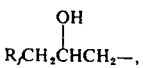

$R_f$ being the same as defined above and $R^6$ is a hydrogen atom; (2) those having the formula (II) in which $x$ is an integer of 3 and $y$ and $z$ are each an integer of 1; (3) those having the formula (II) in which $R^2$ is —(CH$_2$)$_2$— and $R^4$ is an alkylene group having 3 to 5 carbon atoms; and (4) those having the formula (II) in which $R_f$ is a perfluoroalkyl group having 9 to 17 carbon atoms.

According to one of preferred processes for producing the present silane derivatives they can be prepared by reacting perfluoroalkylpropylene epoxides having the formula

(III)

wherein $R_f$ is the same as defined before with aminoalkyl silane derivatives having the formula

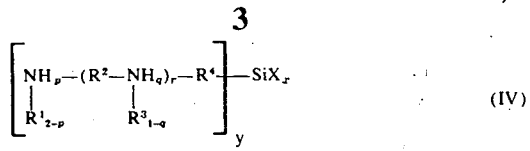

(IV)

wherein $R^1$, $R^2$, $R^3$, $R^4$, X, p, q, r, x and y are the same as defined above.

In the above reaction the epoxy group contained in the epoxide (III) is reacted with one or more of the hydrogen atoms of amino groups in the aminoalkyl silane derivative (IV) to produce the present compound. Therefore, it is preferable to use the epoxide (III) in an approximately stoichiometric amount, depending on the desired compound (I) to be obtained. The reaction can be usually conducted at a temperature of 20° to 200°C, preferably 80° to 150°C, under atmospheric pressure. If necessary, organic solvents inert to the reaction can be used. Examples thereof are ethyl formate, butyl formate, amyl formate, ethyl acetate, butyl acetate and like esters, ethyl ether, isopropyl ether, n-butyl ether, dichloroethylether, anisol, dioxane, tetrahydrofuran and like ethers, carbon tetrachloride, trichloromethane, trichloroethane, tetrachloroethane and like chlorohydrocarbons, trichlorotrifluoroethane, dichlorotetrafluoroethane, tetrachlorodifluoroethane, chlorodifluoromethane, dichlorofluoromethane, and like chlorofluorohydrocarbons, acetone and like ketones having 2 to 6 carbon atoms. The silane derivative (I) thus obtained can be separated from the resulting reaction mixture by conventional methods, for example, by recrystallization.

The epoxides (III) to be used as a starting material are known compounds and can be easily prepared, for example, by reacting an iodine containing alcohol having the formula $R_fCH_2CHICH_2OH$ wherein $R_f$ is the same as defined before with an aqueous solution of alkali metal hydroxide at an elevated temperature. Preferable epoxides (III) are those having the formula (III) in which $R_f$ is a perfluoroalkyl group having 9 to 17 carbon atoms and examples thereof are as follows:

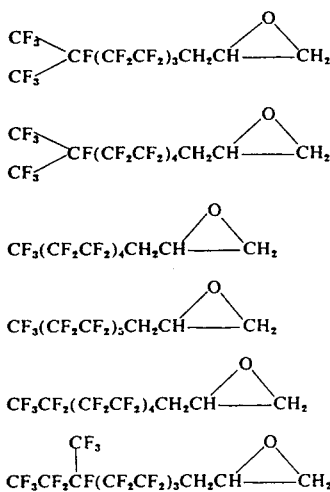

Another starting material, aminoalkyl silane derivative (IV) is also known and can be produced, for example, by reacting a trichlorosilane of the formula $HSiCl_3$ with an ω-chloro-alkene-1 of the formula $Cl(CH_2)_{n-2}CH=CH_2$, wherein n is an integer of 1 to 5, to produce an ω-chloro- trichlorosilico alkane of $Cl(CH_2)_nSiCl_3$, n being the same as defined above, reacting the ω-chloro-trichlorosilico alkane with an aliphatic alcohol of the formula $C_mH_{2m+1}OH$, m being 1 to 5, to produce a ω-chloroalkyl silane derivative of $Cl(CH_2)_nSi(OC_mH_{2m+1})_3$, n and m being the same as defined above, and then reacting the ω-chloroalkyl silane derivative with an amine of $H_2N(CH_2CH_2NH)_tH$, t being 2 to 5, to produce the desired aminoalkyl silane derivative (IV) of the formula $H_2N(CH_2CH_2NH)_t(CH_2)_nSi(OC_mH_{2m+1})_3$, n, m and t being the same as defined above. The aminoalkyl silane derivative (IV) can also be obtained by reacting the above chloroalkyl silane derivative of the formula $Cl(CH_2)_nSi(OC_mH_{2m+1})_3$, n and m being the same as defined above, with ammonia to produce the desired aminoalkyl silane derivatives (IV) of the formula $H_2N(CH_2)_nSi(OC_mH_{2m+1})_3$, n and m being the same as defined above. Preferable aminoalkyl silane derivatives (IV) are those having the formula

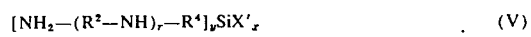   (V)

wherein $R^2$, $R^4$, r, y and x are the same as defined before and X' is an alkoxyl group having 1 to 5 carbon atoms or an alkyl group having 1 to 5 carbon atoms and at least one of groups represented by X' is an alkoxyl group having 1 to 5 carbon atoms. The most preferable are (1) those having the above formula (V) in which x is an integer of 3 and y is an integer of 1 and (2) those having the above formula (V) in which $R^2$ is —$(CH_2)_2$— and $R^4$ is an alkylene group having 3 to 5 carbon atoms. Examples thereof are as follows:

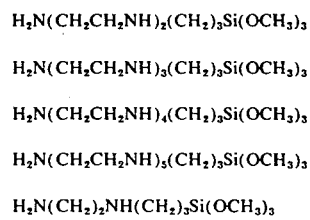

The present silane derivatives (I) are solid or greasy substances at room temperature and soluble in ketones having alkyl groups of 1 to 7 carbon atoms such as acetone, methylethyl ketone, etc., ethers such as dioxane, tetrahydrofuran, etc., and chlorofluorohydrocarbons such as trichlorofluoromethane, trichlorotrifluoroethane, tetrachlorodifluoroethane, etc., but insoluble in methanol, benzene, heptane, etc. The silane derivatives (I) per se of the invention are excellent in stability and the organic solvent solution thereof is also stable. The stability of the solution increases in proportion to the number of carbon atoms of the perfluoroalkyl group ($R_f$) contained in the present silane derivative (I).

As disclosed above, the silane derivative (I) of the present invention can easily be prepared by reacting the epoxide (III) with the aminoalkyl silane derivative (IV) and have a property capable of imparting excellent durable water- and oil-repellency with a high anti-friction property not only to fibrous materials but also to non-porous materials. It is known in the art that water- and oil-repellent compound can be prepared from the epoxide (III). However, according to the known method the epoxide (III) is reacted with acrylic acid (or methacrylic acid) to produce 2-hydroxy-1,1,2,3,3-pentahydroperfluoroalkyl acrylate (or methacrylate) and then the resulting acrylate (or methacrylate) is subjected to emulsion polymerization to obtain water- and oil-repellent compound. According to this method, not only two steps of reactions, i.e., esterification reaction and polymerization reaction are necessary but also the resulting compound fails to impart durable water- and oil-repellency having antifriction property to non-porous materials.

The present silane derivative (I) is mixed with a carrier such as an organic solvent to prepare a water- and oil-repellent composition. According to one of preferred methods at least one of the present compounds (I) is dissolved in an organic solvent to produce solution-type composition. The concentration thereof is preferably in the range of 0.1 to 20 weight percent. The composition can be applied to an article by various methods, for example, by dipping, coating, spraying, etc., followed by drying, whereby excellent durable water- and oil-repellent coating having a high order of antifriction property can be formed on the article.

The articles to be treated include not only porous materials such as paper, cloth, leather and like fibrous materials but also non-porous materials such as products of steel, aluminum, copper and like metal, glass, polyethylene, polyvinylchloride, polypropylene, polyacrylate, polymethacrylate, polystyrene, polyurethane and like plastics, etc. Particularly, it is to be noted that the present compound (I) can impart excellent durable water- and oil-repellency having a high antifriction property to non-porous inorganic materials. For example, when windshield glass of aeroplane is treated with the present water- and oil-repellent composition, it exhibits excellent water- and oil-repellency for a long period of time free from adherance of water-droplets which will make visibility poor. Further, when the inner surface of a glass bottle is treated with the present composition, the liquid contained therein can be completely taken out therefrom without leaving any droplets of the liquid.

For a better understanding of the invention examples are given below.

EXAMPLE 1

In a 100-ml four-necked glass flask equipped with a stirrer, thermometer and reflux condenser were placed 52.6 g (0.1 mole) of

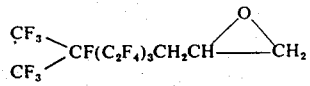

and 22.2 g (0.1 mole) of $H_2N(CH_2)_2NH(CH_2)_3Si(OCH_3)_3$. The mixture was heated with stirring at 80°C. After 2 hours the peaks of both starting materials were found to have disappeared completely by gas chromatography. The mixture was further heated at 80°C for 1 hour. The reaction mixture was cooled to room temperature to obtain solid substance. Recrystallization from the solution of the solid substance in a 1 : 1 weight ratio mixture of trichlorotrifluoroethane and carbon tetrachloride gave 45.3 g of

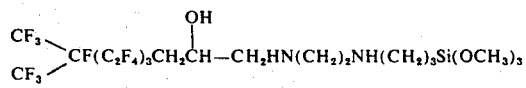

as a waxy solid, white in color.

The product was easily soluble in trichlorotrifluoroethane and carbon tetrachloride, but hardly soluble in chloroform. Elementary analysis of the product gave the following results:

|        | F     | C     | N    | Si   |
|--------|-------|-------|------|------|
| Found  | 48.2% | 31.9% | 3.6% | 3.8% |
| Calcd. | 48.3% | 32.1% | 3.7% | 3.8% |

Infrared absorption analysis gave absorptions completely different from both starting materials. For example, the absorption at 3000 to 3100 cm$^{-1}$ due to the presence of epoxy group of the starting epoxide disappeared.

EXAMPLE 2

In the same flask as in example 1 were placed 52.6 g (0.1 mole) of

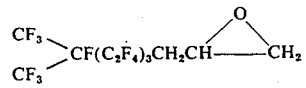

and 11.1 g (0.05 mole) of $H_2N(CH_2)_2NH(CH_2)_3Si(OCH_3)_3$. The mixture was heated with stirring at 80°C. After 4 hours the peaks of both starting materials were found to have disappeared by gas chromatography. Thereafter, the mixture was further heated at 80°C for 1 hour. The resulting reaction mixture was dissolved in trichlorotrifluoroethane, and chloroform was added dropwise to the solution for reprecipitation, whereby 52.8 g of

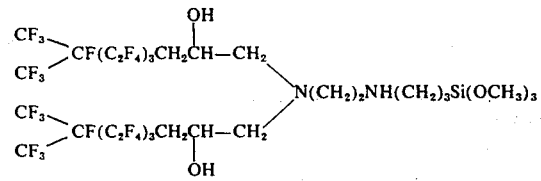

was obtained as a waxy solid, white in colour. The product thus obtained was found to be a single compound by programed temperature gas chromatography.

The product was easily soluble in trichlorotrifluoroethane, tetrachlorodifluoroethane and carbon tetrachloride, but hardly soluble in chloroform. Elementary analysis of the product gave the following results:

|        | F     | C     | N    | Si   |
|--------|-------|-------|------|------|
| Found  | 56.5% | 30.5% | 2.3% | 2.0% |
| Calcd. | 56.7% | 30.1% | 2.2% | 2.2% |

EXAMPLE 3

In the same flask as in example 1 were placed 100 g of an epoxide mixture shown below, 19 g (0.0855 mole) of $H_2N(CH_2)_2NH(CH_2)_3Si(OCH_3)_3$ and 100 g of a 9 : 1 weight ratio mixture of $CCl_2FCCl_2F$ and $CClF_2CClF_2$.

The epoxide mixture used:
1. Formula

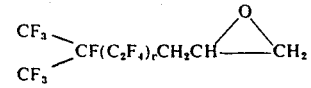

wherein $v$ is an integer of 3 to 7.

2. Composition

| $v$ | wt% | mole |
|---|---|---|
| 3 | 55 | 0.1045 |
| 4 | 26 | 0.0416 |
| 5 | 12 | 0.0165 |
| 6 | 5 | 0.0061 |
| 7 | 2 | 0.0022 |
| Total | 100 | 0.1709 |

The resulting starting mixture was heated with stirring at 70°C. After 8 hours the peaks of both starting materials were found to have disappeared completely by gas chromatography. Thereafter, the mixture was further heated at 80°C for 1 hour and then treated in the same manner as in example 2, whereby 112 g of

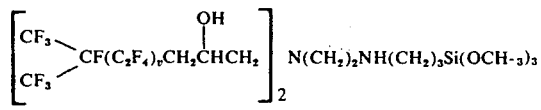

$v$ being the same as above, was obtained as a waxy solid, white in colour. The product was easily soluble in trichlorotrifluoroethane, tetrachlorodifluoroethane and carbon tetrachloride, but hardly soluble in chloroform.

EXAMPLE 4

100 g of the same epoxide mixture as in example 3 was reacted with 38 g (0.171 mole) of $H_2N(CH_2)_2NH(CH_2)_3Si(OCH_3)_3$ in the same manner as in example 1, except that the reaction was conducted at 90°C. After 2 hours the peaks of both starting materials were found to have disappeared completely by gas chromatography. Thereafter, the mixture was further heated at 80°C for 1 hour and treated in the same manner as in example 2, whereby 127 g of

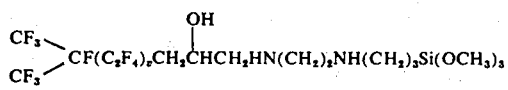

$v$ being the same as defined above, was obtained as a waxy solid, white in color. The product was easily soluble in trichlorotrifluoroethane, tetrachlorodifluoroethane and carbon tetrachloride, but hardly soluble in chloroform.

Each of the products obtained in examples 1 to 4 was dissolved in trichlorotrifluoroethane to prepare four kinds of water- and oil-repellent compositions containing the product in a concentration of 1 wt.%. A glass plate was washed with water, degreased with methanol and then with trichlorotrifluoroethane and dried. The cleaned glass plate was dipped in each composition and dried in air for 30 minutes.

Contact angle, relative to water and to n-hexadecane, of each glass plate thus treated was measured at 25°C, using a goniometer (Erma Contact Anglometer, Goniometer Type, Model G-I, M-2010A, product of Erma Kogaku K.K., Japan). Further, the glass plate thus treated was rubbed 100 times with a 5-cm stroke with polyester-cotton blended cloth wrapped round an iron piece having a diameter of 5 cm and weighing 500 g, the cloth being replaced by new one every 10 strokes. Thereafter the contact angle thereof was measured in the same manner as above.

For comparison, two glass plates were respectively treated in the same manner as above using a 1 wt.% trichlorotrifluoroethane solution of 2-hydroxy-1,1,2,3,3-pentahydroperfluoroalkyl methacrylate polymer (comparison 1) and a 1 wt.% trichlorotrifluoroethane solution of $H_2N(CH_2)_2NH(CH_2)_3Si(OCH_3)_3$ (comparison 2). Contact angle of each glass plate thus obtained was measured in the same manner as above.

The results are shown in Table 1 below:

Table 1

| Sample | Contact angle (degrees) | | | |
|---|---|---|---|---|
| | Before rubbing | | After rubbing | |
| | Water | n-Hexadecane | Water | n-Hexadecane |
| Contrast (Untreated) | 85 | Less than 10 | — | — |
| Example 1 | 98 | 67 | 100 | 65 |
| Example 2 | 103 | 66 | 101 | 66 |
| Example 3 | 104 | 72 | 107 | 71 |
| Example 4 | 105 | 73 | 107 | 72 |
| Comparison 1 | 104 | 72 | 90 | 45 |
| Comparison 2 | 90 | Less than 10 | — | — |

EXAMPLE 5

In a 100-ml four-necked glass flask equipped with a stirrer, thermometer and reflux condenser were placed 52.6 g (0.1 mole) of

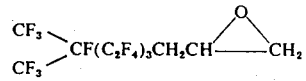

and 14.6 g (0.05 mole) of

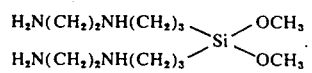

The resulting mixture was heated with stirring at 80°C for 3 hours. By gas chromatography the peaks of both starting materials were found to have disappeared completely. The reaction mixture was cooled and recrystallized in the same manner as in example 1, whereby 64.7 g of

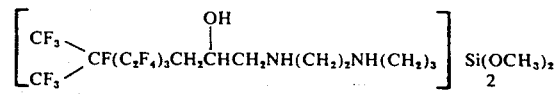

was obtained as a waxy solid, white in color. The product was easily soluble in trichlorotrifluoroethane, tetrachlorodifluoroethane and carbon tetrachloride, but hardly soluble in chloroform. The elementary analysis of the product gave the following results:

|        | F     | C     | N    | Si   |
|--------|-------|-------|------|------|
| Found  | 53.5% | 31.8% | 4.3% | 2.0% |
| Calcd. | 53.7% | 32.1% | 4.2% | 2.1% |

EXAMPLE 6

In the same manner as in example 5 were reacted 52.6 g (0.1 mole) of

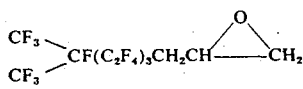

and 20.6 g (0.1 mole) of

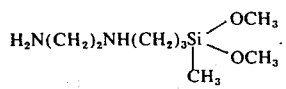

The resulting reaction mixture was cooled and recrystallized in the same manner as in example 1, whereby 68.3 g of

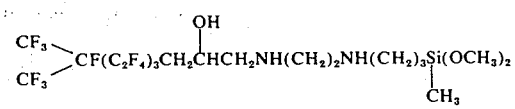

was obtained as a waxy solid, white in color.

The product was easily soluble in trichlorotrifluoroethane, tetrachlorodifluoroethane and carbon tetrachloride, but hardly soluble in chloroform. The elementary analysis of the product gave the following results:

|        | F     | C     | N    | Si   |
|--------|-------|-------|------|------|
| Found  | 49.2% | 33.2% | 3.6% | 3.9% |
| Calcd. | 49.3% | 32.8% | 3.8% | 3.8% |

EXAMPLE 7

In the same manner as in example 5 were reacted 52.6 g (0.1 mole) of

and 35.1 g (0.1 mole) of H₂N(CH₂CH₂NH)₄(CH₂)₃Si(OCH₃)₃, except that the reaction temperature was 100°C. The resulting reaction mixture was cooled and recrystallized in the same manner as in example 1, whereby 83.5 g of

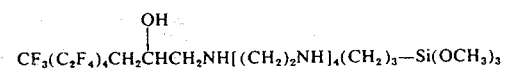

was obtained as a waxy solid, white in colour. The product was easily soluble in trichlorotrifluoroethane, tetrachlorodifluoroethane and carbon tetrachloride but hardly soluble in chloroform. Elementary analysis thereof gave the following results:

|        | F     | C     | N    | Si   |
|--------|-------|-------|------|------|
| Found  | 40.9% | 34.7% | 7.9% | 3.2% |
| Calcd. | 41.2% | 35.6% | 8.0% | 3.2% |

EXAMPLE 8

In the same manner as in example 5 were reacted 52.6g (0.1 mole) of

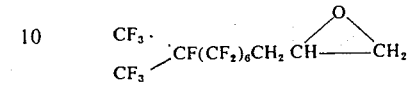

and 20.7 g (0.1 mole) of NH₂(CH₂)₅Si(OCH₃)₃. The resulting reaction mixture was cooled and recrystallized in the same manner as in example 1, whereby 70.4 g of

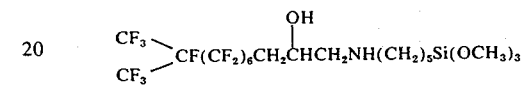

was obtained as a waxy solid, white in colour. The product was easily soluble in trichlorotrifluoroethane, tetrachlorodifluoroethane and carbon tetrachloride but hardly soluble in chloroform. The elementary analysis thereof gave the following results:

|        | F     | C     | N    | Si   |
|--------|-------|-------|------|------|
| Found  | 48.8% | 32.1% | 2.0% | 3.7% |
| Calcd. | 49.2% | 32.7% | 1.9% | 3.8% |

EXAMPLE 9

32.6 g (0.1 mole) of

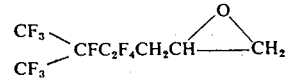

and 32.0 g (0.1 mole) of

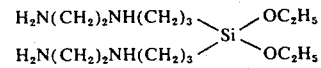

were reacted in the same manner as in example 1. The resulting reaction mixture was cooled and recrystallized in the same manner as in example 1, whereby 61.2 g of

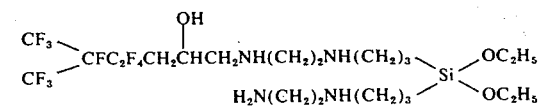

was obtained as a waxy solid, white in colour.

The product was easily soluble in trichlorotrifluoroethane, tetrachlorodifluoroethane and carbon tetrachloride but hardly soluble in chloroform. Elementary analysis thereof gave the following results:

|        | F     | C     | N    | Si   |
|--------|-------|-------|------|------|
| Found  | 31.8% | 40.8% | 8.5% | 4.3% |
| Calcd. | 32.4% | 40.9% | 8.7% | 4.3% |

EXAMPLE 10

32.6 g (0.1 mole) of

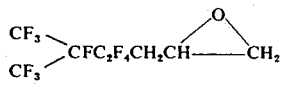

and 16.0 g (0.05 mole) of

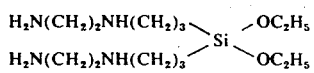

were reacted in the same manner as in example 5. The resulting reaction mixture was cooled and recrystallized same manner as in example 1, whereby 44.1 g of

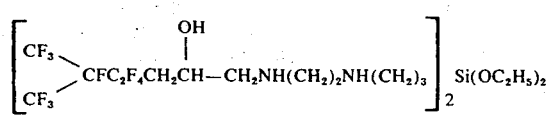

was obtained as a waxy solid, white in colour.

The product was easily soluble in trichlorotrifluoroethane, tetrachlorodifluoroethane and carbon tetrachloride, but hardly soluble in chloroform. Elementary analysis thereof gave the following results:

|        | F     | C     | N    | Si   |
|--------|-------|-------|------|------|
| Found  | 42.7% | 36.9% | 6.0% | 2.9% |
| Calcd. | 43.0% | 37.0% | 5.8% | 2.9% |

Water- and oil-repellency of the compounds obtained in examples 5 to 10 were determined in the same manner as disclosed before with the results shown in Table 2 below.

Table 2

| Sample | Contact angle (degrees) | | | |
|---|---|---|---|---|
| | Before rubbing | | After rubbing | |
| | Water | n-Hexadecane | Water | n-Hexadecane |
| Example 5 | 104 | 68 | 102 | 67 |
| Example 6 | 101 | 67 | 103 | 66 |
| Example 7 | 101 | 66 | 101 | 66 |
| Example 8 | 103 | 69 | 102 | 67 |
| Example 9 | 97 | 59 | 95 | 57 |
| Example 10 | 101 | 63 | 100 | 62 |

What we claim is:

1. A hydroxypolyfluoroalkyl-containing silane derivative having the formula $$\left[ \begin{array}{c} NH_p-(R^2-NH_q)_r-R^4 \\ | \quad\quad | \\ R^1_{2-p} \quad\quad R^3_{1-q} \end{array} \right]_{y-z} SiX_r$$
$$Z_z$$

wherein each of $R^1$ and $R^3$ is an alkyl group having 1 to 5 carbon atoms; each of $R^2$ and $R^4$ is an alkylene group having 1 to 5 carbon atoms; X is an alkoxyl group having 1 to 5 carbon atoms, alkyl group having 1 to 5 carbon atoms, hydroxyl group, chlorine atom or hydrogen atom and at least one of the groups represented by X is an alkoxyl group having 1 to 5 carbon atoms, hydroxyl group, chlorine atom or hydrogen atom; $p$ is zero or an integer of 1 or 2, $q$ is zero or an integer of 1, $r$ is zero or an integer of 1 to 5, $y$ is an integer of 1 or 2 and $x$ is an integer of 2 or 3, provided that the sum of $p$ and $qr$ is at least 1 and the sum of $x$ and $y$ is 4; $z$ is an integer of 1 or 2 equal to or less than that represented by $y$; and Z is a group represented by $$\begin{array}{c} R_p^5 \quad\quad R_q^6 \\ | \quad\quad\quad | \\ N-(R^2-N)_r-R^4- \\ | \quad\quad\quad | \\ R^1_{2-p} \quad\quad R^3_{1-q} \end{array}$$

wherein $R^1$, $R^2$, $R^3$, $R^4$, $p$, $q$ and $r$ are the same as defined above and each of $R^5$ and $R^6$ is a hydrogen atom or $$\begin{array}{c} OH \\ | \\ R_fCH_2CHCH_2- \end{array}$$

and at least one of the groups represented by $R^5$ and $R^6$ is $$\begin{array}{c} OH \\ | \\ R_fCH_2CHCH_2-, \end{array}$$

$R_f$ being a perfluoroalkyl group having 3 to 21 carbon atoms; each of said $R^2$, $R^4$, $R^5$, $R^6$ and X being different or same when plural in number.

2. The hydroxypolyfluoroalkyl-containing silane derivative having the formula

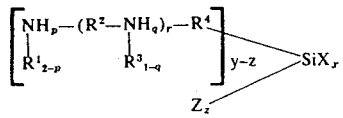

wherein each of $R^2$ and $R^4$ is an alkylene group having 1 to 5 carbon atoms; X' is an alkoxyl group having 1 to 5 carbon atoms or alkyl group having 1 to 5 carbon atoms and at least one of the groups represented by X' is an alkoxyl group having 1 to 5 carbon atoms; $r$ is zero or an integer of 1 to 5, $y$ is an integer of 1 or 2 and $x$ is an integer of 2 or 3, provided that the sum of $x$ and $y$ is 4; $z$ is an integer of 1 or 2 equal to that represented by y; and each of $R^5$, $R^6$ and $R^7$ is a hydrogen atom or

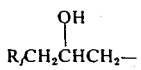

and at least one of the groups represented by $R^5$, $R^6$ and $R^7$ is

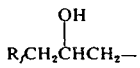

$R_f$ being a perfluoroalkyl group having 3 to 21 carbon atoms.

3. The hydroxypolyfluoroalkyl-containing silane derivative according to claim 2, in which at least one of the groups represented by said $R^5$ and $R^7$ is

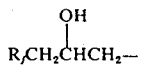

$R_f$ being a perfluoroalkyl group having 3 to 21 carbon atoms, and said $R^6$ is a hydrogen atom.

4. The hydroxypolyfluoroalkyl-containing silane derivative according to claim 2, in which said $x$ is an integer of 3 and $y$ and $z$ are each an integer of 1.

5. The hydroxypolyfluoroalkyl-containing silane derivative according to claim 2, in which said $R^2$ is $-(CH_2)_2-$ and said $R^4$ is an alkylene group having 3 to 5 carbon atoms.

6. The hydroxypolyfluoroalkyl-containing silane derivative according to claim 2, in which said $R_f$ is a perfluoroalkyl group having 9 to 17 carbon atoms.

7. A process for producing a hydroxypolyfluoroalkyl-containing silane derivative, which comprises reacting a perfluoroalkylpropylene epoxide having the formula

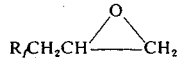

wherein $R_f$ is a perfluoroalkyl group having 3 to 21 carbon atoms with an aminoalkyl silane derivative having the formula

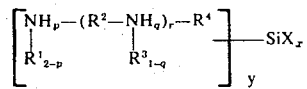

wherein each of $R^1$ and $R^3$ is an alkyl group having 1 to 5 carbon atoms; each of $R^2$ and $R^4$ is an alkylene group having 1 to 5 carbon atoms; X is an alkoxyl group having 1 to 5 carbon atoms, alkyl group having 1 to 5 carbon atoms, hydroxyl group, chlorine atom or hydrogen atom and at least one of the groups represented by X is an alkoxyl group having 1 to 5 carbon atoms, hydroxyl group, chlorine atom or hydrogen atom; and $p$ is zero or an integer of 1 or 2, $q$ is zero or an integer of 1, $r$ is zero or an integer of 1 to 5, $y$ is an integer of 1 or 2 and $x$ is an integer of 2 or 3, provided that the sum of $p$ and $qr$ is at least 1 and the sum of $x$ and $y$ is 4; each of said $R^2$, $R^4$ and X being different or same when plural in number.

8. The process according to claim 7, in which said $R_f$ of the epoxide is a perfluoroalkyl group having 9 to 17 carbon atoms.

9. The process according to claim 7, in which said epoxide is one species selected from the group consisting of

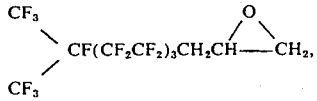

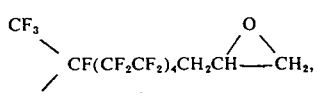

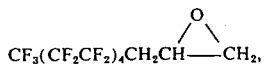

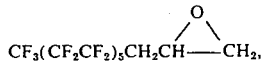

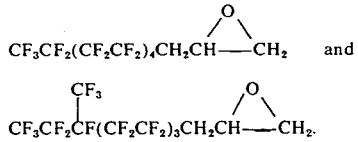 and

10. The process according to claim 7, in which said amino-alkyl silane derivative has the formula $$[NH_2-(R^2-NH)_r-R^4]_y SiX'_x$$

wherein each of $R^2$ and $R^4$ is an alkylene group having 1 to 5 carbon atoms; X' is an alkoxyl group having 1 to 5 carbon atoms or an alkyl group having 1 to 5 carbon atoms and at least one of the groups represented by X' is an alkoxy group having 1 to 5 carbon atoms; $r$ is zero or an integer of 1 to 5, $y$ is an integer of 1 or 2 and $x$ is an integer of 2 or 3, provided that the sum of $x$ and $y$ is 4.

11. The process according to claim 10, in which said $x$ is an integer of 3 and $y$ is an integer of 1.

12. The process according to claim 10, in which said $R^2$ is $-(CH_2)_2-$ and $R^4$ is an alkylene group having 3 to 5 carbon atoms.

13. The process according to claim 7, in which said aminoalkyl silane derivative is one species selected from the group consisting of

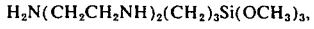

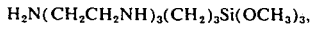

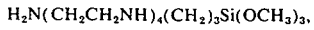

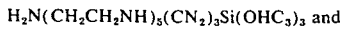 and

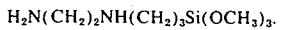

* * * * *